(12) United States Patent
Appukuttan et al.

(10) Patent No.: US 10,941,251 B2
(45) Date of Patent: Mar. 9, 2021

(54) SILICONE POLYMER AND COMPOSITION COMPRISING THE SAME

(71) Applicant: Momentive Performance Materials Inc., Waterford, NY (US)

(72) Inventors: Vinu Krishnan Appukuttan, Bangalore (IN); Pranabesh Dutta, Bangalore (IN); Sandeep Naik, Bangalore (IN); Anubhav Saxena, Bangalore (IN); Masanori Takanashi, Gunma Prefecture (JP)

(73) Assignee: Momentive Performance Materials Inc., Waterford, NY (US)

( * ) Notice: Subject to any disclaimer, the term of this patent is extended or adjusted under 35 U.S.C. 154(b) by 0 days.

(21) Appl. No.: 15/928,469

(22) Filed: Mar. 22, 2018

(65) Prior Publication Data

US 2019/0292321 A1    Sep. 26, 2019

(51) Int. Cl.

| | | |
|---|---|---|
| C08G 77/38 | (2006.01) |
| C08G 77/392 | (2006.01) |
| C08G 77/388 | (2006.01) |
| C08K 3/00 | (2018.01) |
| C08K 3/20 | (2006.01) |
| C08K 3/36 | (2006.01) |
| C08K 3/22 | (2006.01) |
| C08K 3/38 | (2006.01) |
| C09K 5/06 | (2006.01) |
| C09D 11/102 | (2014.01) |
| C08K 7/00 | (2006.01) |
| C08K 7/18 | (2006.01) |
| A61Q 19/00 | (2006.01) |
| A61K 8/899 | (2006.01) |
| A61K 8/02 | (2006.01) |

(Continued)

(52) U.S. Cl.
CPC ............ *C08G 77/392* (2013.01); *A61K 8/025* (2013.01); *A61K 8/0254* (2013.01); *A61K 8/19* (2013.01); *A61K 8/26* (2013.01); *A61K 8/899* (2013.01); *A61Q 19/00* (2013.01); *C08G 77/38* (2013.01); *C08K 3/22* (2013.01); *C08K 3/38* (2013.01); *C08K 7/00* (2013.01); *C08K 7/18* (2013.01); *C09D 11/102* (2013.01); *C09K 5/066* (2013.01); *A61K 2800/10* (2013.01); *A61K 2800/244* (2013.01); *C08G 77/70* (2013.01); *C08G 77/80* (2013.01); *C08K 2003/2227* (2013.01); *C08K 2003/382* (2013.01); *C08K 2003/385* (2013.01); *C08K 2201/001* (2013.01); *C08K 2201/005* (2013.01)

(58) Field of Classification Search
CPC ...... C08G 22/38; C08G 77/70; C08G 77/392; C08K 2003/2227
See application file for complete search history.

(56) References Cited

U.S. PATENT DOCUMENTS 3,176,034 A * 3/1965 Clark .................... C08G 77/00 556/444
3,668,273 A    6/1972 Krantz
(Continued)

FOREIGN PATENT DOCUMENTS

| CN | 102634212 | 8/2012 |
| CN | 103849356 | 6/2014 |

(Continued)

OTHER PUBLICATIONS

Shen et al., "Polyethylene nanofibers with very high thermal conductivities." Nature Nanotechnology, 2010, vol. 5 (4), pp. 251-255.
(Continued)

*Primary Examiner* — Caixia Lu
(74) *Attorney, Agent, or Firm* — Joseph Waters; McDonald Hopkins LLC

(57) ABSTRACT

Provided is a composition comprising:
(A) a silicone polymer of the Formula (I):

$$M^1_a M^2_b M^3_c D^1_d D^2_e D^3_f T^1_g T^2_h T^3_i Q_j.$$

wherein:
  $M^1 = R^1 R^2 R^3 SiO_{1/2}$
  $M^2 = R^4 R^5 R^6 SiO_{1/2}$
  $M^3 = R^7 R^8 R^9 SiO_{1/2}$
  $D^1 = R^{10} R^{11} SiO_{2/2}$
  $D^2 = R^{12} R^{13} SiO_{2/2}$
  $D^3 = R^{14} R^{15} SiO_{2/2}$
  $T^1 = R^{16} SiO_{3/2}$
  $T^2 = R^{17} SiO_{3/2}$
  $T^3 = R^{18} SiO_{3/2}$
  $Q = SiO_{4/2}$
where $R^1, R^2, R^3, R^5, R^6, R^8, R^9, R^{10}, R^{11}, R^{13}, R^{15}, R^{16}$ are independently chosen from a hydrogen, a $C_1$-$C_{60}$ aliphatic or aromatic group or $C_1$-$C_{60}$ alkoxy group;
$R^4, R^{12}, R^{17}$ are independently chosen from a C1-C10 alkyl, a C1-C10 alkoxy, or $R^{19}$-A-$R^{20}$— where A is chosen from a group comprising an unsaturated cyclic moiety chosen from an aromatic group, a fused aromatic group, an unsaturated alicyclic group, an unsaturated heterocyclic group, or a combination of two or more thereof; $R^{19}$ is chosen from a —H, a C1-C10 alkyl, allyl, vinyl, alkoxy, allyloxy, vinyloxy, acrylate, or methacrylate; and $R^{20}$ is chosen from a divalent organic group;
$R^7, R^{14}, R^{18}$ are independently selected from hydrogen or $OR^{22}$ or unsaturated monovalent radicals or radicals containing heteroatom such as oxygen, nitrogen, sulfur or radicals containing organosilane groups; and
the subscripts a, b, c, d, e, f, g, h, i, j are zero or positive subject to the following limitations: $2 \le a+b+c+d+e+f+g+h+i+j \le 1000$, $b+e+h > 0$ and $c+f+i \ge 0$ and
B) a thermally conductive filler.

36 Claims, No Drawings

(51) Int. Cl.
*A61K 8/26* (2006.01)
*A61K 8/19* (2006.01)
*C08G 77/00* (2006.01)

(56) References Cited

U.S. PATENT DOCUMENTS

| | | | |
|---|---|---|---|
| 4,180,515 | A | 12/1979 | Bargain et al. |
| 4,226,761 | A | 10/1980 | Cooper et al. |
| 4,725,658 | A | 2/1988 | Thayer et al. |
| 4,774,028 | A | 9/1988 | Imai et al. |
| 4,814,392 | A | 3/1989 | Shea et al. |
| 5,035,927 | A | 7/1991 | Chen et al. |
| 5,204,438 | A | 4/1993 | Snow et al. |
| 5,357,022 | A | 10/1994 | Banach et al. |
| 5,380,527 | A | 1/1995 | Legrow et al. |
| 5,596,048 | A | 1/1997 | Blohm et al. |
| 5,916,952 | A | 6/1999 | Romenesko et al. |
| 6,783,692 | B2 | 8/2004 | Bhagwagar |
| 6,815,486 | B2 | 11/2004 | Bhagwagar et al. |
| 6,869,642 | B2 | 3/2005 | Freuler et al. |
| 7,074,490 | B2 | 7/2006 | Feng et al. |
| 7,109,288 | B2 | 9/2006 | Akatsuka et al. |
| 7,579,425 | B2 | 8/2009 | Terry et al. |
| 8,921,507 | B2 | 12/2014 | Yoshihara et al. |
| 9,209,104 | B2 | 12/2015 | Nguyen et al. |
| 2003/0096919 | A1 | 5/2003 | Ichinohe |
| 2004/0163556 | A1* | 8/2004 | Kugo ............... B65C 9/1803 101/226 |
| 2004/0254275 | A1* | 12/2004 | Fukui ............... C08L 83/04 524/261 |
| 2007/0051773 | A1 | 3/2007 | Ruchert et al. |
| 2007/0149703 | A1 | 6/2007 | Caprasse et al. |
| 2007/0149834 | A1 | 6/2007 | Endo et al. |
| 2007/0208144 | A1 | 9/2007 | Delsman et al. |
| 2008/0057325 | A1 | 3/2008 | Sakurai et al. |
| 2008/0302064 | A1 | 12/2008 | Rauch |
| 2010/0027672 | A1 | 2/2010 | Chujoh et al. |
| 2011/0272119 | A1 | 11/2011 | Bhagwagar et al. |
| 2012/0322940 | A1 | 12/2012 | Mueller et al. |
| 2018/0163113 | A1 | 6/2018 | Uta et al. |
| 2019/0144752 | A1 | 5/2019 | Hannington et al. |

FOREIGN PATENT DOCUMENTS

| | | |
|---|---|---|
| CN | 105018043 | 11/2015 |
| EP | 0163495 | 12/1985 |
| EP | 2562200 | 2/2013 |
| JP | 11323162 | 11/1999 |
| JP | 2007051221 | 3/2007 |
| JP | 2008214599 | 9/2008 |
| JP | 6125221 | 5/2017 |
| WO | 2015022998 | 2/2015 |
| WO | 2017213809 | 12/2017 |
| WO | 2017002489 | 3/2018 |

OTHER PUBLICATIONS

Singh et al., "High thermal conductivity of chain-oriented amorphous polythiophene." Nature Nanotechnology, 2014, vol. 9, pp. 384-390.

Patent Cooperation Treaty (PCT), International Search Report and Written Opinion for Application PCT/US2019/022251 filed Mar. 14, 2019, dated May 29, 2019, International Searching Authority, EP.

* cited by examiner

SILICONE POLYMER AND COMPOSITION COMPRISING THE SAME

FIELD

The present invention relates to compositions comprising a functionalized siloxane polymer comprising unsaturated cyclic moieties that exhibits thermoplastic and elastomeric properties over a wide range of temperatures and demonstrates reversible phase change behavior with improved physical properties and thermal conducting composition of the same.

BACKGROUND

As modern electronic devices are getting faster, smaller, and thinner, the application of advanced thermal conductive materials has become increasingly important at the interface of different heat generating components such as, for example, transistors, IC chip, engine control units, microprocessor, etc. Such materials enable highly dense and heavily integrated electronic devices to operate smoothly by dissipating heat to the atmosphere. In order to dissipate the heat effectively from the electronic components, various thermally conductive silicone compositions have been employed over the years. Most of these thermal conductive silicone compositions consist of organopolysiloxanes as a binder and heat conducting inorganic fillers.

Owing to better thermal performance, thermal greases are extensively used for high thermal conductivity application. As the power output increases, thermal grease are subjected to extreme thermal cycling leading to dry-out of thermal interface material (TIM) or pump-out of the TIM from interface weakening the thermal management. Phase change thermal interface materials based on soft thermoplastic waxes are recently explored to address this issue. Even though organic based materials are extensively used in such applications, they are limited by lower thermal stability. Hence, there exists a need for low melting thermally stable soft waxy materials. Silicone polymers are known to have higher thermal stability but generally have elastomeric property.

One common method to make silicone thermoplastic composition is by blending siloxane polymer with thermoplastic polymer or by using fillers. However, such techniques may have poor storage stability and phase separation issues. Other techniques used to make solid silicone is through silicone resins by incorporating tertiary (T) and quaternary (Q) silicone group or by cross-linking, but the technique will result in thermoset. Both methods are generally marred by it challenges in post-processing and application methods. Soft thermoplastic silicones could be made through simple organic modification of silicones or through co-polymerization. U.S. Publication 2003/0096919, U.S. Pat. Nos. 4,725,658, 7,579,425 describe the incorporation of long chain hydrocarbons in the form of fatty acid, 1-olefins to the silicone chain to make soft thermoplastic silicones. CN 201410102937 and U.S. Publication 2008/0302064 depict the concept of a phase change silicone composition that uses long chain aliphatic paraffinic waxes, silicone copolymer with aliphatic hydrocarbon, and poyolefins.

SUMMARY

Provided is an organosiloxane copolymer composition with improved thermal conductivity. The composition provides improved thermal conductivity at lower filler loading. Methods of making thermally conducting compositions are disclosed.

In particular, functionalized siloxane polymers present in the composition include grafting of arylene ethers in silicone polymers or resin to impart crystalline segments in the polymer matrix. The arylene ether groups may be placed pendant to the siloxane chain or at the terminal ends of the chain/matrix. The polymers may be curable or non-curable and may include a reactive/curable group terminal or pendant to the siloxane main chain.

In one aspect of the invention, functionalized siloxane polymers exhibit improved thermal conductivity. The polymer may find use in making of thermal conducting composition when combine with thermal fillers. The composition may exhibit enhanced thermal conductivity without incorporating larger quantity of thermal filler such that the post cure properties of a material formed from the polymer is not significantly affected.

In one aspect of the invention, the functionalized siloxane polymer composition have phase change characteristics and exhibit reversible thermoplastic elastomeric properties over a wide range of temperatures.

In one aspect of the invention, there is provided as phase change thermally conducting composition, wherein the phase change characteristics is provided by the reversible thermoplastic elastomeric properties of the functionalized siloxane polymers over a wide range of temperatures. The phase change nature of the composition may be tuned by controlling aspects of the polymer including, for example, the molecular weight of the polymer, the ratio of the various siloxane units (i.e., the M, D, T, and Q units), the concentration of the arylene ether groups, etc.

In one aspect, provided is composition comprising:
(A) a silicone polymer of the Formula (I):

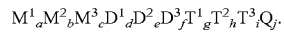

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are independently chosen from a hydrogen, a $C_1$-$C_{60}$ aliphatic or aromatic group or $C_1$-$C_{60}$ alkoxy group;

$R^4$, $R^{12}$, $R^{17}$ are independently chosen from a C1-C10 alkyl, a C1-C10 alkoxy, or $R^{19}$-A-$R^{20}$— where A is chosen from a group comprising an unsaturated cyclic moiety chosen from an aromatic group, a functionalized aromatic group, a fused aromatic group optionally containing a heteroatom, an unsaturated alicyclic group, an unsaturated heterocyclic group, or a combination of two or more thereof; $R^{19}$ is chosen from a —H, a C1-C10 alkyl or allyl or aryl or vinyl optionally containing heteroatom(s), acrylate, or methacrylate; and $R^{20}$ is chosen from a divalent organic group;

$R^7$, $R^{14}$, $R^{18}$ are independently selected from hydrogen or $OR^{22}$ or unsaturated monovalent radicals or radicals containing heteroatom such as oxygen, nitrogen, sulfur or radicals containing organosilane groups; and the subscripts a, b, c, d, e, f, g, h, i, j are zero or positive subject to the following limitations: 2≤a+b+c+d+e+f+g+h+i+j≤1000, b+e+h>0 and c+f+i≥0;

B) a thermally conductive filler;
C) optionally an antioxidant;
D) optionally an inhibitor;
E) optionally a volatile diluent;
F) optionally a coupling agent.

In one embodiment, A is chosen from a group of the formula -A-R$^{21}$-A$^2$- where A$^1$ and A$^2$ are independently chosen from a C6 to C12 aryl group, C12-C36 fused aromatic ring group, a C5-C36 unsaturated alicyclic group, and a C5-C36 unsaturated heterocyclic group; and R$^{21}$ is chosen from a direct bond, —(CH$_2$)$_n$—, —C(CH$_3$)$_2$—, —O—, —S—, —S(O)$_2$—, —C(O)—, C(O)—NH—, —NH—C(O)—NH—, C(O)—O—, —CH=N—, or —CH=N—N=CH— where n is 1-10.

In one embodiment, A is independently chosen from

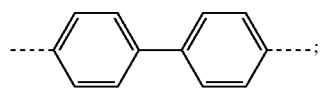 (A-i)

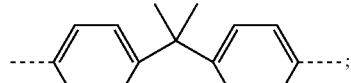 (A-ii)

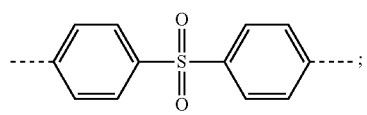 (A-iii)

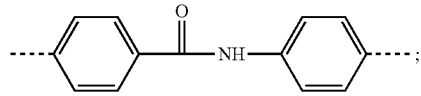 (A-iv)

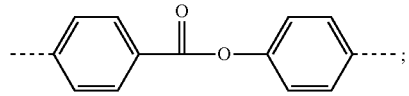 (A-v)

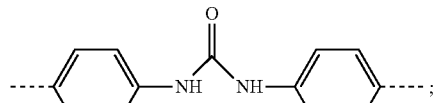 (A-vi)

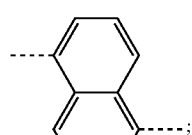 (A-vii)

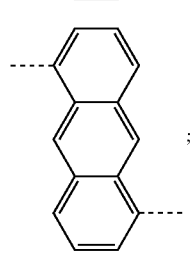 (A-viii)

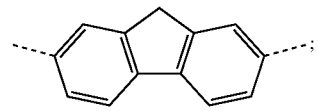 (A-ix)

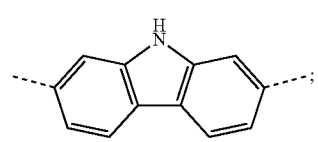 (A-x)

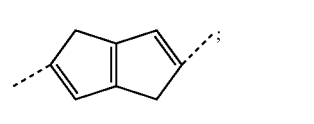 (A-xi)

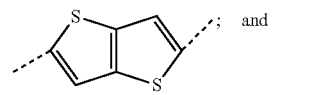 (A-xii)

and

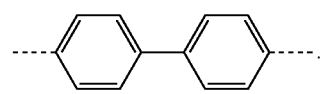 (A-xiii)

In one embodiment, A in R$^4$, R$^{12}$ and R$^{17}$ is

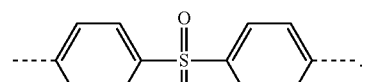

In one embodiment, R$^{19}$ is CH$_2$=CH$_2$—(CH$_2$)l-O— and l is 0 or 1.

In one embodiment, R$^1$, R$^2$, R$^3$, R$^5$, R$^6$, R$^8$, R$^9$, R$^{10}$, R$^{11}$, R$^{13}$, R$^{15}$, R$^{16}$ are methyl.

In one embodiment, A in R$^4$, R$^{12}$ and R$^{17}$ is

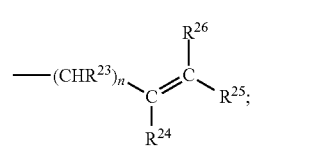

In one embodiment, R$^{19}$ is chosen from —H, CH$_2$=CH$_2$—(CH$_2$)$_l$—, CH$_2$=CH$_2$—(CH$_2$)$_l$—O— where l is 0-10; and R$^{20}$ is chosen from a C2-C10 bivalent alkyl group, —O—(CH$_2$)m-, or —O—C(O)—(CH2)$_m$-, and m is 2-10.

In one embodiment according to any previous embodiment, the A containing group is pendant to the siloxane chain.

In one embodiment, the unsaturated monovalent radical in the present invention can be selected from the group of the formulae (I) to (V)

$$—(CHR^{23})_n\underset{R^{24}}{\overset{}{C}}=\underset{R^{25}}{\overset{R^{26}}{C}} \quad (I)$$

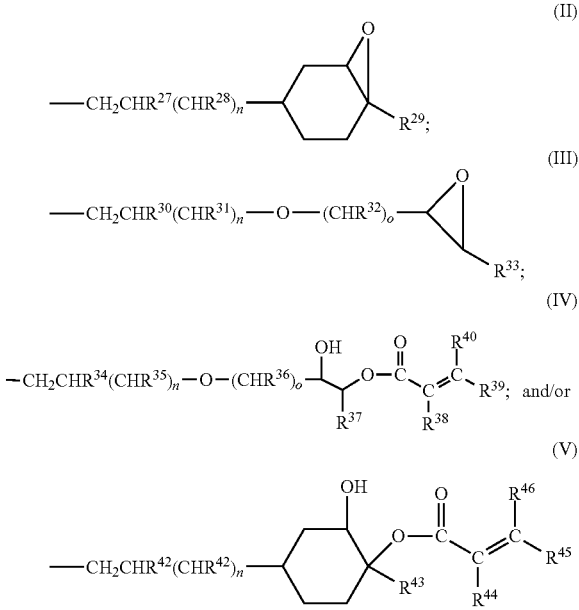

wherein $R^{23}$, $R^{28}$, $R^{31}$, $R^{32}$, $R^3$, $R^{36}$, $R^{42}$ are independently selected from —H, —OH, alkyl, alkenyl, cycloalkyl, aryl and aliphatic/aromatic monovalent hydrocarbon having from 1 to 60 carbon atoms; $R^{22}$, $R^{24}$, $R^{25}$, $R^{26}$, $R^{27}$, $R^{29}$, $R^{30}$, $R^{33}$, $R^{34}$, $R^{37}$, $R^{38}$, $R^{39}$, $R^{40}$, $R^{41}$, $R^{43}$, $R^{44}$, $R^{45}$, $R^{46}$ are independently selected from hydrogen or aliphatic/aromatic monovalent hydrocarbon having from 1 to 60 carbon atoms; the subscript n is zero or positive integer and has a value in the range of 0 to 6; subscript o is positive integer and has a value in the range of 1 to 6.

In one embodiment of the composition according to any previous embodiment, the polymer has a number average molecular weight ($M_n$) of from about 400 g/mol to about 100000 g/mol.

In one embodiment of the composition according to any previous embodiment, the filler material is chosen from alumina, magnesia, ceria, hafnia, lanthanum oxide, neodymium oxide, samaria, praseodymium oxide, thoria, urania, yttria, zinc oxide, zirconia, silicon aluminum oxynitride, borosilicate glasses, barium titanate, silicon carbide, silica, boron carbide, titanium carbide, zirconium carbide, boron nitride, silicon nitride, aluminum nitride, titanium nitride, zirconium nitride, zirconium boride, titanium diboride, aluminum dodecaboride, barytes, barium sulfate, asbestos, barite, diatomite, feldspar, gypsum, hormite, kaolin, mica, nepheline syenite, perlite, phyrophyllite, smectite, talc, vermiculite, zeolite, calcite, calcium carbonate, wollastonite, calcium metasilicate, clay, aluminum silicate, talc, magnesium aluminum silicate, hydrated alumina, hydrated aluminum oxide, silica, silicon dioxide, titanium dioxide, glass fibers, glass flake, clays, exfoliated clays, or other high aspect ratio fibers, rods, or flakes, calcium carbonate, zinc oxide, magnesia, titania, calcium carbonate, talc, mica, wollastonite, alumina, aluminum nitride, graphite, graphene, aluminum powder, copper powder, bronze powder, brass powder, fibers or whiskers of carbon, graphite, silicon carbide, silicon nitride, alumina, aluminum nitride, zinc oxide, carbon nanotubes, boron nitride nanosheets, zinc oxide nanotubes, or a combination of two or more thereof.

In one embodiment of the composition according to any previous embodiment, the filler material has a mean particle size of from about 0.01 µm to about 500 µm.

In one embodiment of the composition according to any previous embodiment, the filler material is chosen from a plurality of filler materials.

In one embodiment of the composition according to any previous embodiment, the filler material is chosen from a first filler having an average particle size from about 0.01 to about 0.9 µm; a second filler having an average particle size of about 1 µm to about 10 µm; a third filler having an average particle size of about 15 µm to about 150 µm and optionally a fourth filler having an average particle size of about 100 µm to about 400 µm.

In one embodiment of the composition according to any previous embodiment, the composition comprises about 10 vol. % to about 90 vol. % of the first filler and about 90 vol. % to about 10 vol. % of the second filler.

In one embodiment of the composition according to any previous embodiment, the filler comprises (i) a first filler, and (ii) a second filler, where at least one of the first filler and/or the second filler comprises a plurality of filler types differing from one another in terms of particle size and/or morphology.

In one embodiment, the first and second filler are independently chosen from a metal oxide filler and a non-oxide filler.

In one embodiment, the non-oxide filler is chosen from a metal boride, a metal carbide, a metal nitride, a metal silicide, carbon black, graphite, expanded graphite, carbon fiber, or graphite fiber or a combination of two or more thereof.

In one embodiment, the plurality of filler types independently have an average particle size of from about 0.3 micron to about 350 micron, the plurality of filler types having average particle sizes different from one another.

In one embodiment, the plurality of filler types have a morphology different from one another, the morphology being chosen from spherical, platelet, agglomerates, spherical agglomerates and graphitic.

In one embodiment, the first filler is chosen from aluminum oxide, and the second filler is chosen from boron nitride. In one embodiment, the aluminum oxide comprises a plurality of filler types. In one embodiment, the plurality of filler types have an average particle size different from one another. In one embodiment, the plurality of filler types have a morphology different from one another. In one embodiment, the aluminum oxide and the boron nitride each comprise the plurality of filler type.

In one embodiment of the composition according to any previous embodiment, the composition has a phase change temperature from 30° C. to 120° C.

In one embodiment of the composition according to any previous embodiment, the composition has a thermal conductivity in the range of 2 to 18 W/m·K.

In one embodiment of the composition according to any previous embodiment, the composition has a thermal stability till 200° C. for 1500 hrs.

In one embodiment of the composition according to any previous embodiment, the composition is in the form of a thermal grease, adhesive, thermal gel, potting material, or a gap filler material.

In another aspect, provided is an article comprising the composition of any previous embodiment, disposed on at least a portion of a surface of the article.

In one embodiment, the article comprises multiple layers, and the composition is disposed on a surface in between at least two of the layers.

In one embodiment of the article according to any previous embodiment, the article is an electronic article, an automotive article, a home appliance article, smart appliance article, a telecommunication article, a healthcare article, a personal care article, an agricultural article, a molded article, a masonry surface, a textile material, a home care material.

In one embodiment of the article according to any previous embodiment, the article comprises light emitting devices, computer devices, a stacked die, mobile phones, tablets, flip chip package, hybrid memory cube, touch screens, Wi-Fi device, automotive technology hifi systems, a through-silicon via device, and audio systems, in joints between heat pipes and water tanks in solar heated heating, in fuel cells and wind turbines, in the manufacture of computer chips, gaming consoles, data transfer devices, in light devices, batteries, in housings, coolers, heat exchanging devices, wires, cables, heating wires, refrigerators, dishwashers, air conditionings, accumulators, transformers, lasers, functional clothing, car seats, medical devices, fire protection, electric motors, planes, and trains, as a filament for 3D printing material, drug delivery systems, transdermal patches, wound healing patches, wound dressing patches, patches for scar reduction, transdermal iontophoresis, scaffold for tissue engineering, anti-microbial devices, wound management devices, ophthalmic devices, bioinserts, prostheses, body implants, paint, structural coating, masonry coating, or marine coating, seed coating, superspreader or controlled release fertilizer.

In still another aspect, provided is a method of preparing the article of any previous embodiment, comprising of dispensing under pressure or stencil printing or screen printing or jet printing or 3D printing.

In one embodiment, thickness of the said composition is from 0.01 mm to 15 cm.

In a further aspect, provided is a personal care product comprising the composition of any previous embodiment.

In one embodiment, the personal care product is in the form of an antiperspirant/deodorant, a shaving product, a skin lotion, a moisturizer, a toner, a bath product, a cleansing product, a shampoo, a conditioner, a combined shampoo/conditioners, a mousse, a styling gel, a hair spray, a hair dye, a hair color product, a hair bleach, a waving products, a hair straightener, a nail polish, a nail polish remover, a nail cream or lotions, a cuticle softener, a sunscreen, an insect repellent, an anti-aging product, a lipstick, a foundation, a face powder, an eye liner, an eye shadow, a blush, a makeup, a mascara, a moisturizing preparation, a foundation, a body and hand preparation, a skin care preparation, a face and neck preparation, a tonic, a dressing, a hair grooming aid, an aerosol fixative, a fragrance preparation, an aftershave, a make-up preparation, a soft focus application, a night and day skin care preparation, a non-coloring hair preparation, a tanning preparation, a synthetic and non-synthetic soap bar, a hand liquid, a nose strip, a non-woven application for personal care, a baby lotion, a baby shampoo, a baby conditioner, a shaving preparation, a cucumber slices, a skin pads, a make-up remover, a facial cleansing product, a cold cream, a sunscreen product, a spritzer, a paste mask and mud, a face mask, a cologne and toilet water, a hair cuticle coat, a shower gel, a face and body wash, a personal care rinse-off products, a gel, a foam bath, a scrubbing cleanser, an astringent, a nail conditioner, an eye shadow stick, a powder for face or eye, a lip balm, a lip gloss, a hair care pump spray, a hair-frizz-control gel, a hair leave-in conditioner, a hair pomade, a hair de-tangling product, a hair fixative, a hair bleach product, a skin lotion, a pre-shave and pre-electric shave, an anhydrous cream and lotion, an oil/water emulsion, a water/oil emulsion, a water-resistant cream or lotion, an anti-acne preparation, a mouth-wash, a massage oil, a toothpaste, a clear gel or stick, an ointment base, a topical wound-healing product, an aerosol talc, a barrier spray, a vitamin and anti-aging preparation, an herbal-extract preparation, a bath salt, a bath and body milk, a hair styling aid, a hair-, eye-, nail- and skin-soft solid application, a controlled-release personal care product, a hair conditioning mist, a skin care moisturizing mist, a skin wipe, a pore skin wipe, a pore cleaner, a blemish reducer, a skin exfoliator, a skin desquamation enhancer, a skin towelette or cloth, a depilatory preparation, or a personal care lubricant.

In still yet another aspect, provided is a process for preparing composition of claim 1 comprising:

a) providing a silicone polymer of Formula (I)

$$M^1_a M^2_b M^3_c D^1_d D^2_e D^3_f T^1_g T^2_h T^3_i Q_j.$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are independently chosen from a hydrogen, a $C_1$-$C_{60}$ aliphatic or aromatic group or $C_1$-$C_{60}$ alkoxy group;

$R^4$, $R^{12}$, $R^{17}$ are independently chosen from a C1-C10 alkyl, a C1-C10 alkoxy, or $R^{19}$-A-$R^{20}$— where A is chosen from a group comprising an unsaturated cyclic moiety chosen from an aromatic group, a fused aromatic group, an unsaturated alicyclic group, an unsaturated heterocyclic group, or a combination of two or more thereof; $R^{19}$ is chosen from a —H, a C1-C10 alkyl, allyl, vinyl, alkoxy, allyloxy, vinyloxy, acrylate, or methacrylate; and $R^{20}$ is chosen from a divalent organic group;

$R^7$, $R^{14}$, $R^{18}$ are independently selected from hydrogen or $OR^{22}$ or unsaturated monovalent radicals or radicals containing heteroatom such as oxygen, nitrogen, sulfur or radicals containing organosilane groups; and the subscripts a, b, c, d, e, f, g, h, i, j are zero or positive subject to the following limitations: $2 \leq a+b+c+d+e+f+g+h+i+j \leq 1000$, $b+e+h>0$ and $c+f+i \geq 0$;

b) optionally add an inhibitor, an antioxidant and a coupling agent; or combination thereof to (a)
c) add a thermally conductive filler to the mixture;
e) optionally add a volatile diluent before or after adding the thermal filler.

DETAILED DESCRIPTION

Reference will now be made to exemplary embodiments, examples of which are illustrated in the accompanying drawings. It is to be understood that other embodiments may be utilized and structural and functional changes may be made. Moreover, features of the various embodiments may be combined or altered. As such, the following description is presented by way of illustration only and should not limit in any way the various alternatives and modifications that may be made to the illustrated embodiments. In this disclosure, numerous specific details provide a thorough understanding of the subject disclosure. It should be understood that aspects of this disclosure may be practiced with other embodiments not necessarily including all aspects described herein, etc.

As used herein, the words "example" and "exemplary" mean an instance, or illustration. The words "example" or "exemplary" do not indicate a key or preferred aspect or embodiment. The word "or" is intended to be inclusive rather than exclusive, unless context suggests otherwise. As an example, the phrase "A employs B or C," includes any inclusive permutation (e.g., A employs B; A employs C; or A employs both B and C). As another matter, the articles "a" and "an" are generally intended to mean "one or more" unless context suggest otherwise.

Provided is a functionalized silicone polymer Also provided is a composition comprising the functionalized silicone polymer and a thermally conductive filler. In particular, provided is a functionalized siloxane polymer. The siloxane polymer comprises organic groups comprising unsaturated cyclic moieties. The present siloxane polymers have been found to exhibit good thermal stability and thermal conductivity with a relatively low filler concentration.

The silicone polymer employed in the compositions is a polymer of Formula (I)

$$M^1_a M^2_b M^3_c D^1_d D^2_e D^3_f T^1_g T^2_h T^3_i Q_j.$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are independently chosen from a hydrogen, a $C_1$-$C_{60}$ aliphatic or aromatic group or $C_1$-$C_{60}$ alkoxy group;

$R^4$, $R^{12}$, $R^{17}$ are independently chosen from a C1-C10 alkyl, a C1-C10 alkoxy, or $R^{19}$-A-$R^{20}$— where A is chosen from a group comprising an unsaturated cyclic moiety chosen from an aromatic group, a fused aromatic group, an unsaturated alicyclic group, an unsaturated heterocyclic group, or a combination of two or more thereof; $R^{19}$ is chosen from a —H, a C1-C10 alkyl, allyl, vinyl, alkoxy, allyloxy, vinyloxy, acrylate, or methacrylate; and $R^{20}$ is chosen from a divalent organic group;

$R^7$, $R^{14}$, $R^{18}$ are independently selected from hydrogen, $OR^{22}$, an unsaturated monovalent radical, a radical containing a heteroatom such as oxygen, nitrogen, sulfur, or a radical containing organosilane groups; and the subscripts a, b, c, d, e, f, g, h, i, and j are zero or positive subject to the limitations that $2 \le a+b+c+d+e+f+g+h+i+j \le 1000$, $b+e+h>0$, and $c+f+i \ge 0$.

As used herein, an unsaturated alicyclic group refers to an aliphatic cyclic group comprising one or more unsaturated bonds. In embodiments, the unsaturated alicyclic group comprises at least one C=C bond. In embodiments, the unsaturated alicyclic group is chosen from a C4-C36 alicyclic group comprising one or more C=C bonds. The unsaturated alicyclic group may comprise a single ring, a fused ring system, or a bicyclic ring system. Non-limiting examples of unsaturated alicyclic compounds include, but are not limited to, cyclopentene, cyclohexene, cyclopentadiene, dicyclopentadiene, etc.

As used herein, an unsaturated heterocyclic group refers to a cyclic group comprising at least one unsaturated bond and at least one heteroatom within the ring structure. The unsaturated group may be a C=C or an unsaturated bond between a carbon atom and a heteroatom.

In embodiments, $R^{19}$ is chosen from —H, $CH_2$=$CH_2$—$(CH_2)_l$—, $CH_2$=$CH_2$—$(CH_2)_l$—O— where l is 0-10; and $R^{20}$ is chosen from a C2-C10 bivalent alkyl group, —O—$(CH_2)_m$-, or —O—C(O)—$(CH2)_m$-, and m is 2-10. In one embodiment, $R^{19}$ is $CH_2$=$CH_2$—$(CH_2)_l$—O— where l is 0. In one embodiment, $R^{19}$ is $CH_2$=$CH_2$—$(CH_2)_l$—O— where l is 1.

In embodiments, A is independently chosen from a divalent C6 to C12 aryl group, a divalent C12 to C36 fused aromatic group, a divalent C4-C36 unsaturated alicyclic group, and a divalent C4-C36 unsaturated heterocyclic group.

In on embodiment, A is chosen from a group of the formula -$A^1$-$R^{21}$-$A^2$- where $A^1$ and $A^2$ are independently chosen from a C6 to C12 aryl group, a C12-C36 fused aromatic ring, a C5-C36 unsaturated alicyclic group, and a C5-C36 unsaturated heterocyclic group; and $R^{21}$ is chosen from a direct bond —$(CH_2)_n$—, —$C(CH_3)_2$—, —O—, —S—, —$S(O)_2$—, —C(O)—, C(O)—NH—, —NH—C(O)—NH—, C(O)—O—, —CH=N—, or —CH=N—N=CH— where n is 1-10. In embodiments, n is 1-6, 1-4, or 1-2.

Examples of suitable groups for the A groups include, but are not limited to:

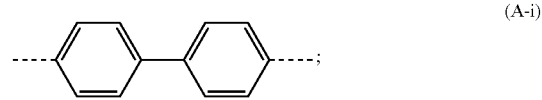

(A-i)

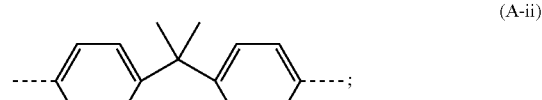

(A-ii)

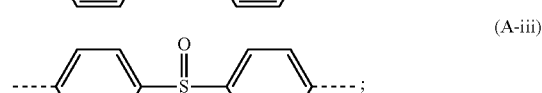

(A-iii)

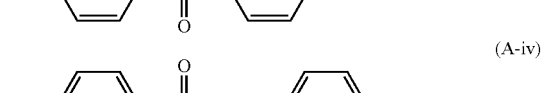

(A-iv)

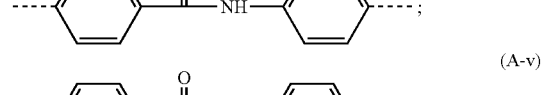

(A-v)

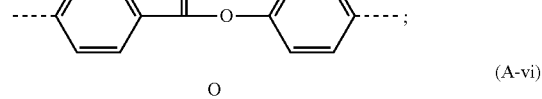

(A-vi)

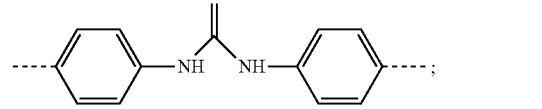

(A-vii)

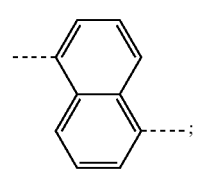

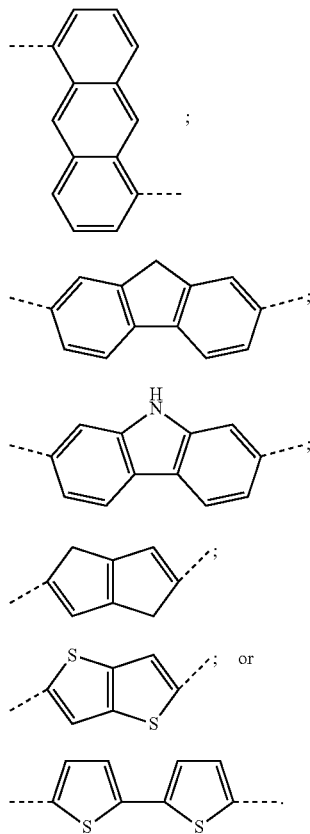

(A-viii)

(A-ix)

(A-x)

(A-xi)

(A-xii) or

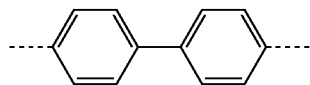

(A-xiii)

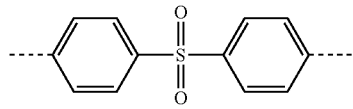

In one embodiment, $R^1$, $R^2$, $R^3$, $R^5$, $R^6$, $R^8$, $R^9$, $R^{10}$, $R^{11}$, $R^{13}$, $R^{15}$, $R^{16}$ are a C1-C4 alkyl, A is

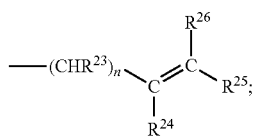

$R^{19}$ is chosen from —H, $CH_2=CH_2-(CH_2)_l-$, $CH_2=CH_2-(CH_2)_l-O-$ where l is 0-10; and $R^{20}$ is chosen from a C2-C10 bivalent alkyl group, $-O-(CH_2)_m-$, or $-O-C(O)-(CH2)_m-$, and m is 2-10. In one embodiment, $R^{19}$ is $CH_2=CH_2-(CH_2)_l-O-$ where l is 0. In one embodiment, $R^{19}$ is $CH_2=CH_2-(CH_2)_l-O-$ where l is 1.

In one embodiment, $R^1$, $R^2$, $R^3$, $R^5$, $R^6$, $R^8$, $R^9$, $R^{10}$, $R^{11}$, $R^{13}$, $R^{15}$, $R^{16}$ are a C1-C4 alkyl, A is

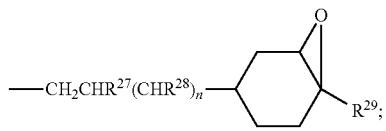

$R^{19}$ is chosen from —H, $CH_2=CH_2-(CH_2)_l-$, $CH_2=CH_2-(CH_2)_l-O-$ where l is 0-10; and $R^{20}$ is chosen from a C2-C10 bivalent alkyl group, $-O-(CH_2)_m-$, or $-O-C(O)-(CH_2)_m-$, and m is 2-10. In one embodiment, $R^{19}$ is $CH_2=CH_2-(CH_2)_l-O-$ where l is 0. In one embodiment, $R^{19}$ is $CH_2=CH_2-(CH_2)_l-O-$ where l is 1.

In one embodiment, A is chosen from any one of (A-i)-(A-xiii), and $R^{19}$—H, $CH_2=CH_2-(CH_2)_l-$, $CH_2=CH_2-(CH_2)_l-O-$ where l is 0-10; and $R^2$ is chosen from a C2-C10 bivalent alkyl group, $-O-(CH_2)_m-$, or $-O-C(O)-(CH2)_m-$, and m is 2-10. In one embodiment A is chosen from any of (A-i)-(A-xiii); $R^{19}$ is chosen from $CH_2=CH_2-(CH_2)_l-O-$ where l is 0 and $R^{20}$ is chosen from $-O-(CH_2)_m-$ where m is 2. In one embodiment A is chosen from any of (A-i)-(A-xiii); $R^{19}$ is chosen from $CH_2=CH_2-(CH_2)_l-O-$ where l is 0 and $R^{20}$ is chosen from $-O-(CH_2)_m-$ where m is 3. In one embodiment A is chosen from any of (A-i)-(A-xiii); $R^{19}$ is chosen from $CH_2=CH_2-(CH_2)_l-O-$ where l is 1 and $R^{20}$ is chosen from $-O-(CH_2)_m-$ where m is 2. In one embodiment A is chosen from any of (A-i)-(A-xiii); $R^{19}$ is chosen from $CH_2=CH_2-(CH_2)_l-O-$ where l is 1 and $R^2$ is chosen from $-O-(CH_2)_m-$ where m is 3.

In embodiments, $R^7$, $R^{14}$, $R^{18}$ are chosen from an unsaturated monovalent radical in the present invention can be selected from the group of the formulae (I) to (V)

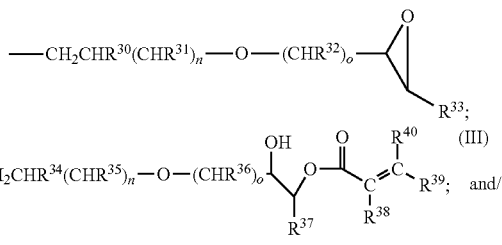

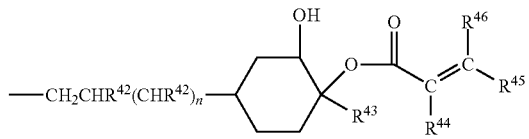

wherein $R^{23}$, $R^{28}$, $R^{31}$, $R^{32}$, $R^{35}$, $R^{36}$, $R^{42}$ are independently selected from —H, —OH, alkyl, alkenyl, cycloalkyl, aryl and aliphatic/aromatic monovalent hydrocarbon having from 1 to 60 carbon atoms; $R^{22}$, $R^{24}$, $R^{25}$, $R^{26}$, $R^{27}$, $R^{29}$, $R^{30}$, $R^{33}$, $R^{34}$, $R^{37}$, $R^{38}$, $R^{39}$, $R^{40}$, $R^{41}$, $R^{43}$, $R^{44}$, $R^{45}$, $R^{46}$ are independently selected from hydrogen or aliphatic/aromatic monovalent hydrocarbon having from 1 to 60 carbon atoms; the subscript n is zero or positive integer and has a value in the range of 0 to 6; subscript o is positive integer and has a value in the range of 1 to 6.

The present polymers may be formed via hydrosilylation of an appropriate unsaturated compound and a silyl hydride in the presence of a catalyst. The unsaturated compounds to provide the $R^4$, $R^{12}$, $R^{17}$ groups may be of the formula $R^{19}$-A-$R^{19'}$ where A is as described above, and $R^{19}$ and $R^{19'}$ are independently chosen from allyl, vinyl, allyloxy, vinyloxy, acrylate, or methacrylate. In embodiments, $R^{19}$ and $R^{19'}$ are independently chosen from $CH_2=CH_2-(CH_2)_a-$, $CH_2=CH_2-(CH_2)_a-O-$, $CH_2=CH_2-(CH_2)_a-C(O)-O-$, where a is 0-10. The silyl hydride may be, for example, a siloxane with terminal silyl hydride functional groups or with a Si—H containing group within the main chain of the siloxane.

Useful catalysts include those compounds or molecules that can catalyze the hydrosilylation reaction between a reactive SiH-containing moiety or substituent and a carbon-carbon bond such as a carbon-carbon double bond. Also, in one or more embodiments, these catalysts may be soluble within the reaction medium. Types of catalysts include transition metal compounds including those compounds that include a Group VIII metal. Exemplary Group VIII metals include palladium, rhodium, germanium, and platinum. Exemplary catalyst compounds include chloroplatinic acid, elemental platinum, chloroplatinic acid hexahydrate, complexes of chloroplatinic acid with sym-divinyltetramethyl-disiloxane, dichloro-bis(triphenylphosphine) platinum (II), cis-dichloro-bis(acetonitrile) platinum (II), dicarbonyldi-chloroplatinum (II), platinum chloride, and platinum oxide, zero valent platinum metal complexes such as Karstedt's catalyst, [Cp*Ru(MeCN)$_3$]PF$_6$, [PtCl$_2$(cyclooctadiene)], solid platinum supported on a carrier (such as alumina, silica or carbon black), platinum-vinylsiloxane complexes (e.g., Pt$_n$(ViMe$_2$SiOSiMe$_2$Vi)$_c$ and Pt[(MeViSiO)$_4$]$_d$)), platinum-phosphine complexes (e.g., Pt(PPh$_3$)$_4$ and Pt(PBU$_3$)$_4$)), and platinum-phosphite complexes (e.g., Pt[P(Oph)$_3$]$_4$ and Pt[P(Obu)$_3$]$_4$)), wherein Me represents methyl, Bu represents butyl, "Vi" represents vinyl and Ph represents phenyl, and c and d represent integers. Others include RhCl(PPh$_3$)$_3$, RhCl$_3$, Rh/Al$_2$O$_3$, RuCl$_3$, IrCl$_3$, FeCl$_3$, AlCl$_3$, PdCl$_2$.2H$_2$O, NiCl$_2$, TiCl$_4$, etc.

The properties or state of the polymer can be controlled or tuned by controlling various aspects of the polymer. In particular, the polymer may be provided as a liquid, a gum, or a solid by controlling the degree of polymerization, silicone chain length, and molecular weight.

In one embodiment, the silicone polymer has a number average molecular weight of from about 400 to about 100000; from about 500 to about 50000; even from about 600 to about 25000. Molecular weight may be determined by GPC.

The polymers exhibit properties that make them useful in a variety of applications. The polymers may exhibit reversible thermoplastic behavior. The polymers possess both plastic and elastomeric properties over a wide range of temperatures. The phase change temperature of the polymers is from about 20° C. to about 120° C. The properties or state of the polymer can be controlled or tuned by controlling various aspects of the polymer. In particular, the polymer may be provided as a liquid, a gum, or a solid by controlling the degree of polymerization, silicone chain length, and molecular weight. The properties, e.g., melting/phase change behavior, may be tuned or selected by the silicone segment (e.g., size or number of m and x units) and the divalent unsaturated cyclic groups A).

The polymers may be used to form a silicone composition. In one embodiment, the silicone composition is provided as a thermal conducting composition comprising the silicone polymer and a thermally conductive filler material. The filler materials for the thermally conductive filler (B) can be chosen from a metal oxide or a non-oxide filler. Examples of suitable non-oxide fillers include a metal boride, a metal carbide, a metal nitride, a metal silicide, carbon black, graphite, expanded graphite, carbon fiber, or graphite fiber or a combination of two or more thereof. Examples of thermally conductive fillers include, but are not limited to, alumina, magnesia, ceria, hafnia, lanthanum oxide, neodymium oxide, samaria, praseodymium oxide, thoria, urania, yttria, zinc oxide, zirconia, silicon aluminum oxynitride, borosilicate glasses, barium titanate, silicon carbide, silica, boron carbide, titanium carbide, zirconium carbide, boron nitride, silicon nitride, aluminum nitride, titanium nitride, zirconium nitride, zirconium boride, titanium diboride, aluminum dodecaboride, barytes, barium sulfate, asbestos, barite, diatomite, feldspar, gypsum, hormite, kaolin, mica, nepheline syenite, perlite, phyrophyllite, smectite, talc, vermiculite, zeolite, calcite, calcium carbonate, wollastonite, calcium metasilicate, clay, aluminum silicate, talc, magnesium aluminum silicate, hydrated alumina, hydrated aluminum oxide, silica, silicon dioxide, titanium dioxide, glass fibers, glass flake, clays, exfoliated clays, or other high aspect ratio fibers, rods, or flakes, calcium carbonate, zinc oxide, magnesia, titania, calcium carbonate, talc, mica, wollastonite, alumina, aluminum nitride, graphite, expanded graphite, metallic powders, e.g., aluminum, copper, bronze, brass, etc., fibers or whiskers of carbon, graphite, silicon carbide, silicon nitride, alumina, aluminum nitride, zinc oxide, nano-scale fibers such as carbon nanotubes, boron nitride nanosheets, zinc oxide nanotubes, etc., and mixtures of two or more thereof. In one embodiment, the thermally conductive filler has a low electrical conductivity or is electrically insulating.

The particle size of the filler materials may be chosen as desired for a particular purpose or intended application. In embodiments, the filler material has an average particle size of from about 0.01 μm to about 500 μm; from about 0.1 to about 250 μm; from about 1 to about 100 μm; from about 5 to about 75 μm; even from about 10 to about 50 μm. It will be appreciated that the composition may comprise a combination of inorganic fillers of different average particle sizes. Such combinations may be chosen as desired for a particular purpose or intended application. In one embodiment, the composition comprises a first organic filler having an average particle size from about 0.01 to about 0.1 μm; a second filler having an average particle size of about 1 μm to about 25 μm; and optionally a third filler having an average particle size of about 50 μm to about 100 μm. The first, second, and third fillers may be the same or different from one another in terms of the chemical makeup of the filler.

In the composition, the silicone polymer may be present in an amount of from about 20 vol. % to about 75 vol. % based on the total volume of the composition. In one embodiment the filler loading is from about 25 vol. % to about 70 vol. % from about 35 vol. % to about 65 vol. %, even from about 40 vol. % to about 60 vol. %. The composition may have total filler concentration, i.e., the concentration of all the fillers in the composition, of from about 25 vol. % to about 80 vol. % based on the total volume of the composition. In one embodiment the filler loading is from about 30 vol. % to about 75 vol. % from about 35 vol. % to about 65 vol. %, even from about 40 vol. % to about 60 vol. %. Here as in the claims, numerical values may be combined to form new and unspecified ranges.

The thermally conductive filler (B) comprises a combination of fillers, where at least one filler material is provided as a plurality of filler types. As used herein, a "filler type" refers to a category of filler material having a particular characteristic. Examples of characteristics defining a filler type include, for example, the morphology of the filler, the particle size of the filler, or the morphology and particle size of the filler. Examples of different embodiments of different filler types include:

a first filler type having a first particle size, and a second filler type having a second particle size, where the first and second filler types have the same morphology a first filler type having a first morphology, and a second filler type having a second morphology, where the first and second filler types have the same particle size;

a first filler type having a first morphology, and a second filler type having a second morphology, where the first and second filler types have different particle sizes.

In the above embodiments, the first and second filler may be a single type of filler or may itself be provided with multiple filler types.

In one embodiment, the first filler and the second filler are each provided by a plurality of filler types of the respective filler materials. The composition may include any combination of a first filler and a second filler, where (i) the first filler is provided by:

a first filler type having a first particle size, and a second filler type having a second particle size, where the first and second filler types have the same morphology;

a first filler type having a first morphology, and a second filler type having a second morphology, where the first and second filler types have the same particle size; or a first filler type having a first morphology, and a second filler type having a second morphology, where the first and second filler types have different particle sizes; and (ii) the second filler is provided by:

a second filler type having a first particle size, and a second filler type having a second particle size, where the first and second filler types have the same morphology;

a second filler type having a first morphology, and a second filler type having a second morphology, where the first and second filler types have the same particle size; or a second filler type having a first morphology, and a second filler type having a second morphology, where the first and second filler types have different particle sizes.

So, for example, in one embodiment, there may be provided (a) a first filler provided by (i) a first filler type having a first particle size, and (ii) a second filler type having a second particle size; and (b) a second filler provided by (i) a first filler type having a first particle size, and (ii) a second filler type having a second particle size. In another embodiment, the composition may comprise (a) a first filler provide by (i) a first filler type having a first particle size, and (ii) a second filler type having a second particle size, where the first and second filler types have the same morphology; and (b) a second filler provided by (i) a first filler type of a first morphology, and (ii) a second filler type of a second morphology.

It will be appreciated that while the above description refers to a first filler and a second filler, the composition is not limited to two fillers. The composition may comprise two, three, four, five, etc., or more fillers, where at least one of the fillers is provided by a plurality of filler types of that filler material. Optionally, each of the fillers may be provided by a plurality of filler types of the respective filler materials.

In one embodiment, the composition comprises a first filler chosen from a metal oxide, and the second filler is chosen from a non-oxide filler (e.g., a nitride, a carbide, a silicide, etc.). In one embodiment, the metal oxide filler is provided as a plurality of filler types of different particle sizes, and the non-oxide filler is provided as a single filler type (e.g., a filler of a particular morphology and particle size). In another embodiment, (a) the metal oxide filler comprises a first filler type of a first particle size and a second filler type of a second particle size; and (b) the non-oxide filler comprises (i) a first filler type of a first morphology, and (ii) a second filler type of a second morphology.

The morphology of the respective fillers may be chosen as desired. In one embodiment, the morphology of the filler may be chosen from spherical, platelet, agglomerates, spherical agglomerates, and graphitic.

In one embodiment, the first and second thermally conductive filler materials have a particle size of 0.3 to about 350 microns. In one embodiment, the thermally conductive filler has a particle size of about 0.5 to 150 microns; about 1 to about 100 microns, about 10 to 90 microns; about 20 to 75 microns; even about 40 to 60 microns.

The composition may have total filler concentration, i.e., the concentration of all the fillers in the composition, of from about 25 vol. % to about 80 vol. % based on the total volume of the composition. In one embodiment the filler loading is from about 30 vol. % to about 75 vol. % from about 35 vol. % to about 65 vol. %, even from about 40 vol. % to about 60 vol. %. Here as in the claims, numerical values may be combined to form new and unspecified ranges.

The composition may comprise from about 10 vol. % to 90 vol. % of the first filler and 90 vol. % to 10 vol. % of the second filler; from about 30 vol. % to 70 vol. % of the first filler and 70 vol. % to 30 vol. % of the second filler; even from about 40 vol. % to about 60 of the first filler and about 60 vol. % to about 40 vol. % of the second filler.

Regarding the different filler types contributing to the first and/or second fillers, the concentration of the different filler types may be chose as desired. In one embodiment, the first filler comprises a first filler type in an amount of about 5 vol. % to about 95 vol. % and a second filler type in an amount of about 95 vol. % to about 5 vol. % based on the total volume of the first filler; a first filler type in an amount of about 10 vol. % to about 80 vol. % and a second filler type in an amount of about 20 vol. % to about 90 vol. % based on the total volume of the first filler; a first filler type in an amount of about 30 vol. % to about 60 vol. % and a second filler type in an amount of about 70 vol. % to about 40 vol. % based on the total volume of the first filler. In one embodiment, the first filler comprises a first filler type in an amount of about 20 vol. % to about 40 vol. % and a second filler type in an amount of about 80 vol. % to about 60 vol. % based on the total volume of the first filler.

In one embodiment, the thermally conductive filler includes a boron nitride. Examples of suitable boron nitride materials include boron nitride particles, boron nitride agglomerates, or a mixture thereof. Boron nitride particles generally exhibit a platelet form. In one embodiment, the boron nitride particles can be platelets having a particle size of 0.3 to about 350 microns. In one embodiment, the platelet boron nitride particles have a particle size of about 0.5 to 150 microns; about 1 to about 100 microns, about 10 to 90 microns; about 20 to 75 microns; even about 40 to 60 microns. In another embodiment, the thermally conductive plastic composition comprises boron nitride agglomerates. The agglomerates can have a mean particle size of from about 5 to about 500 microns and a surface area of about 0.25 to about 50 m$^2$/gram. In one embodiment, the platelet boron nitride particles have a particle size of about 10 to 400 microns; about 20 to about 300 microns; about 30 to 200 microns; about 40 to 150 microns; even about 50 to 100 microns. Particle size can be measured using a Horiba LA300 particle size distribution analyzer where the particle to be analyzed (e.g., BN) is introduced in an amount adjusted to meet the required transmission. A few drops of 2% Rhodapex CO-436 can be added to improve the dispersion of the powder, and the particle size can be measured using laser diffraction after a 3 second sonication. The particle size distribution resulting from the measurement can be plotted on a volume basis and the D90 represents the 90$^{th}$ percentile of the distribution.

In one embodiment, the filler may be functionalized with a functionalization additive such as, for example, a silane additive. In one embodiment, the silane additive can be chosen from an alkoxy silane, alkacryloxy silane, a vinyl silane, a halo silane (e.g., a chlorosilane), a mercapto silane, a blocked mercaptosilane, a thiocarboxylate silane, or a combination of two or more thereof. In one embodiment, the fillers can comprise from about 1 to about 5 wt. % of a silane; from about 1.5 to about 4 wt. %; even from about 2.7 to about 3.7 wt. % of the fillers.

In one embodiment, the composition comprises a first filler chosen from a metal oxide, and a second filler chosen from a non-oxide filler where the first filler and/or the second filler comprises a plurality of filler types. In one embodiment, the first filler is a metal oxide comprising a first type of metal oxide and a second type of metal oxide, which may be the same or different metal oxide in terms of chemical make up, and the second filler comprises a single type of non-oxide filler, where any of the following (alone or in combination) may be employed:

the first type of metal oxide has a first particle size, and the second type of metal oxide has a second particle size different from the first particle size;

the first and second type of metal oxide independently have a particle size of from about 0.3 to about 350 microns, where the first and second type of metal oxide have a different particle size;

the first type of metal oxide has a first morphology, and the second type of metal oxide has a second morphology different from the first morphology;

the metal oxide filler is chosen from alumina, magnesia, ceria, hafnia, lanthanum oxide, neodymium oxide, samaria, praseodymium oxide, thoria, urania, yttria, zinc oxide, and/or zirconia;

the non-metal oxide filler is chosen from silicon carbide, silica, boron carbide, titanium carbide, zirconium carbide, boron nitride, silicon nitride, aluminum nitride, titanium nitride, zirconium nitride, or zirconium boride;

the first filler is alumina, and the second filler is boron nitride;

the second filler is a boron nitride chosen from spherical, platelet, agglomerates, or spherical agglomerates.

In one embodiment, the composition comprises a first filler chosen from a metal oxide, and a second filler chosen from a non-oxide filler where the first filler and the second filler each comprises a plurality of filler types. In one embodiment, the first filler is a metal oxide comprising a first type of metal oxide and a second type of metal oxide, where the first and second type of metal oxide may have the same or different chemical composition or formula (but differ at least in respect of particle size and/or morphology), and the second filler comprises a single type of non-oxide filler, where any of the following may be employed in combination with one another:

the first type of metal oxide has a first particle size, and the second type of metal oxide has a second particle size different from the first particle size;

the first and second type of metal oxide independently have a particle size of from about 0.3 to about 350 microns, where the first and second type of metal oxide have a different particle size;

the first type of metal oxide has a first morphology, and the second type of metal oxide has a second morphology different from the first morphology;

the first type of metal oxide has a first particle size, and the second type of metal oxide has a second particle size different from the first particle size;

the metal oxide filler is chosen from alumina, magnesia, ceria, hafnia, lanthanum oxide, neodymium oxide, samaria, praseodymium oxide, thoria, urania, yttria, zinc oxide, and/or zirconia;

the non-metal oxide filler is chosen from silicon carbide, silica, boron carbide, titanium carbide, zirconium carbide, boron nitride, silicon nitride, aluminum nitride, titanium nitride, zirconium nitride, or zirconium boride;

the first filler is alumina, and the second filler is boron nitride;

the second filler comprises platelet boron nitride and boron nitride agglomerates.

In one embodiment, the composition comprises a first filler having a first filler type of a particle size of from about 0.3 to about 350 microns, and a second filler type having a particle size of from about 0.3 to about 350 microns, where the second filler type of the first filler has a different particle size from the first filler type. In one embodiment, the composition comprises a first filler with a first filler type having a particle size of from about 0.3 to about 350 microns, and a second filler type having a particle size of from about 0.3 to about 15 microns. In one embodiment, the composition comprises a first filler having a first filler type with a particle size of from about 45 to about 350 microns and a second filler type having a particle size of form about 0.3 to about 5 microns. In one embodiment, the composition comprises a first filler with a first filler type having a particle size of from about 5 to about 70 microns, and a second filler type having particle size of from about 0.5 to about 15 microns. In one embodiment, the first filler comprises alumina.

The composition may further comprise an addition or condensation curing catalyst. The present compositions are curable and may be cured by either condensation curing mechanisms or thermal curing mechanisms. In one embodiment, the compositions are condensation curable. For a condensation curable composition, the composition may include any suitable components to promote condensation curing. The composition may optionally comprise a condensation catalyst which promotes the condensation of completely or partially hydrolyzed topcoat material. The catalyst can be a catalyst suitable for promoting the curing of siloxanes. Advantageously, condensation catalysts can be employed. Suitable condensation catalysts include, but are not limited to, dialkyltin dicarboxylates such as dibutyltin dilaurate and dioctyltin dilaurate, tertiary amines, the stannous salts of carboxylic acids, such as stannous octoate and stannous acetate, etc. Other useful catalysts include zirconium-containing, aluminum-containing, and bismuth-containing complexes such as K-KAT® XC6212, K-KAT® 5218 and K-KAT® 348, supplied by King Industries, Inc., titanium chelates such as the TYZOR® types, available from DuPont company, and the KR types, available from Kenrich Petrochemical, Inc., and other organometallic catalysts, e.g., those containing a metal such as Al, Zn, Co, Ni, Fe, etc.

Generally, the catalyst should be added in an amount that will not affect or impair the physical properties of the composition, but in a sufficient amount to catalyze the curing reaction. In one embodiment, the catalyst is provided in an amount ranging from 1 ppm to about 75 ppm; from about 10 ppm to about 70 ppm; even from about 20 ppm to about 60 ppm. Here, as elsewhere in the specification and claims, numerical values may be combined to form new and non-disclosed ranges. The "ppm" value of the catalyst may be defined as total moles of catalyst per total weight solid of the composition.

The present compositions are curable and may be cured by either condensation curing mechanisms or thermal curing mechanisms. In one embodiment, the compositions are condensation curable. For a condensation curable composition, the composition may include any suitable components to promote condensation curing. The composition may optionally comprise a condensation catalyst which promotes the condensation of completely or partially hydrolyzed topcoat material. The catalyst can be a catalyst suitable for promoting the curing of siloxanes. Advantageously, condensation catalysts can be employed. Suitable condensation catalysts include, but are not limited to, dialkyltin dicarboxylates such as dibutyltin dilaurate and dioctyltin dilaurate, tertiary amines, the stannous salts of carboxylic acids, such as stannous octoate and stannous acetate, etc. Other useful catalysts include zirconium-containing, aluminum-containing, and bismuth-containing complexes such as K-KAT® XC6212, K-KAT® 5218 and K-KAT® 348, supplied by King Industries, Inc., titanium chelates such as the TYZOR® types, available from DuPont company, and the KR types, available from Kenrich Petrochemical, Inc., and other organometallic catalysts, e.g., those containing a metal such as Al, Zn, Co, Ni, Fe, etc.

In one embodiment, the compositions are thermal curable and comprise a thermal cure catalyst. In one embodiment, the thermal cure catalyst is chosen from an alkyl ammonium carboxylate. The alkyl ammonium carboxylate may be a di-, tri-, or tetra-ammonium carboxylate. In one embodiment, the catalyst is chosen from a tetrabutylammonium carboxylate of the formula: $[(C_4H_9)_4N]^+[OC(O)—R]^-$, wherein R is selected from the group consisting of hydrogen, alkyl groups containing about 1 to about 8 carbon atoms, and aromatic groups containing about 6 to 20 carbon atoms. In embodiments, R is a group containing about 1 to 4 carbon atoms, such as methyl, ethyl, propyl, butyl, and isobutyl. Exemplary catalysts are tetra-n-butylammonium acetate (TBAA), tetra-n-butylammonium formate, tetra-n-butylammonium benzoate, tetra-n-butylammonium-2-ethylhexanoate, tetra-n-butylammonium-p-ethylbenzoate, and tetra-n-butylammonium propionate, or a combination of two or more thereof. Particularly suitable catalysts are tetra-n-butylammonium acetate and tetra-n-butylammonium formate, tetramethylammonium acetate, tetramethylammonium benzoate, tetrahexylammonium acetate, dimethylanilium formate, dimethylammonium acetate, tetramethylammonium carboxylate, tetramethylammonium-2-ethylhexanoate, benzyltrimethylammonium acetate, tetraethylammonium acetate, tetraisopropylammonium acetate, triethanol-methylammonium acetate, diethanoldimethylammonium acetate, monoethanoltrimethylammonium acetate, ethyltriphenylphosphonium acetate.

Generally, the catalyst should be added in an amount that will not affect or impair the physical properties of the coating, but in a sufficient amount to catalyze the curing reaction. In one embodiment, the catalyst is provided in an amount ranging from 1 ppm to about 75 ppm; from about 10 ppm to about 70 ppm; even from about 20 ppm to about 60 ppm. Here, as elsewhere in the specification and claims, numerical values may be combined to form new and non-disclosed ranges. The "ppm" value of the catalyst may be defined as total moles of catalyst per total weight solid of the coating.

The current phase change thermally conducting composition may contain a coupling agent as optional component. In one embodiment, provided is a composition of any previous embodiment, wherein the fillers are treated with a coupling agent chosen from an alkoxy silane, an alkoxy siloxane, an alkoxy cyclic siloxane, an alkoxy oragno-siloxane, an alkoxy cyclic oragno-siloxane, an alkacryloxy silane, a vinyl silane, a halo silane (e.g., a chlorosilane), a mercapto silane, a blocked mercaptosilane, a thiocarboxylate silane, titanate salts, zirconate salts, or a combination of two or more thereof.

In the composition, the coupling agent may be present in an amount of up to 20 wt % based on the total weight of composition. In one embodiment the coupling agent loading is from about 0.1 wt % to about 10 wt %, or from about 0.5 wt % to about 8 wt %.

The current phase change thermally conducting composition may contain volatile diluent as an optional component. In yet another embodiment, the volatile diluents are chosen from an aliphatic hydrocarbon, a cyclic hydrocarbon, an aromatic hydrocarbon, a cyclic siloxane, a linear siloxane or a combination of two or more thereof. The volatile diluents may have linear, branched or cross-linked structure. The volatile diluents may be saturated or unsaturated. Examples of volatile diluents are hydrocarbons of carbon chain length of 5 to 14, paraffin oils, isoparaffins, toluenes, xylenes, cyclohexane, C6-C14 linear and internal olefins, petroleum ether, halogenated hydrocarbons, heteroatom containing hydrocarbons, octamethylcyclotetrasiloxane, decamethylcyclotetrasiloxane siloxane, hexamethyldisiloxane and thereof.

In the composition, the volatile diluent be present in an amount of up to 30 wt % based on the total weight of composition. In one embodiment, the diluent is present from about 0.1 wt % to about 20 wt %, from about 0.5 wt % to about 10 wt %.

The current phase change thermally conducting composition may contain antioxidant as an optional component. In yet another embodiment, the antioxidant are chosen from a phosphate type, phenolic type antioxidant, a thio-ether type antioxidant, an amine type antioxidant, or a combination of two or more thereof.

In the composition, the antioxidant be present in an amount of up to 10 wt % based on the total weight of composition. In one embodiment, the antioxidant loading is from about 0.05 wt % to about 10 wt %, from about 0.1 wt % to about 5 wt %.

The present polymers and compositions have been found to exhibit desirable properties that may make them suitable for a wide variety of applications. The polymers have high thermal stability, refractive index, and thermal conductivity. The have excellent wetting behavior when combined with inorganic fillers such that the fillers are readily dispersed in the polymer. These properties allow for providing a composition with excellent thermal conductivity. The composition exhibits phase change characteristics. The composition is a solid at room temperature (about 20° C. to about 25° C.). The compositions are also characterized by a softening temperature in the range of about 25° C. to about 100° C., where it could be spread.

In embodiments, the compositions of the present invention may also find use as a thixotropic agent or a rheology modifying agent. A "thixotropic agent" as used herein is one that increases the thixotropy of the composition in which it is contained, promoting shear thinning and enabling use of reduced injection force.

The compositions may be used in a variety of applications and may be applied by a variety of methods including, for example, printing, dispensing, and/or spraying onto a substrate.

What has been described above includes examples of the present specification. It is, of course, not possible to describe every conceivable combination of components or methodologies for purposes of describing the present specification, but one of ordinary skill in the art may recognize that many further combinations and permutations of the present specification are possible. Accordingly, the present specification is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

EXAMPLES

The bulk thermal conductivity (T/C) is determined, unless mentioned otherwise in the examples, by transient method using Hot Disk TPS 500 S instrument. Number-average molecular weight ($M_n$) and poly dispersity index (PDI), with reference to monodisperse polystyrene standards, were determined using Agilent 1260 Infinity gel permeation chromatography system equipped with solvent degasser, Agilent Mixed-BLS (10 um) column, ELSD and RID detector. Melting point was determined by Differential Scanning Calorimetry (DSC) on a TA Instrument Inc. (Q 1000) at a heating rate of 10° C. min$^{-1}$ under a nitrogen atmosphere.

Synthesis Examples

Example 1: Diphenyl Sulfone Functionalized Polyorganosiloxane Bearing Terminal Allyloxy Ether Group (A1)

A three-necked flask was charged with 10 g of 4,4'-Diallyloxy diphenylsulfone, Toluene (50 mL) and platinum catalyst (10 ppm). The resulting mixture was heated to 90° C. while stirring under nitrogen atmosphere and adding 12.7 g of polydimethylsiloxane having terminal dimethylhydrogensiloxy units and consisting of approximately 10 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as waxy solid (GPC: $M_n$=2200 g/mol; PDI=1.3). The polymer has a T/C of 0.195 W/m·K. and peak melting point of 79.5° C.

Example 2: Diphenyl Sulfone Functionalized Polyorganosiloxane Bearing Terminal Allyloxy Ether Group (A2)

A three-necked flask was charged with 10 g of 4,4'-Diallyloxy diphenylsulfone, Toluene (50 mL) and platinum catalyst (10 ppm). The resulting mixture was heated to 90° C. while stirring under nitrogen atmosphere and adding 18 g of polydimethylsiloxane having terminal trimethyl units and consisting of approximately 20 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as waxy solid (GPC: $M_n$=3000 g/mol; PDI=1.4) which has peak melting point of 57° C.

Example 3: Biphenyl Functionalized Polyorganosiloxane Bearing Q Structure (A3)

A three-necked flask was charged with 35.5 g of 4-(allyloxy)-1,1'-biphenyl, toluene (90 mL) and platinum catalyst (15 ppm). The resulting mixture was heated to 72° C. while stirring under nitrogen atmosphere and adding 15 g of polydimethylsiloxane having approximately 4 Q units and approximately 8 units of dimethylhydrogensiloxy. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane resin as white solid (GPC: $M_n$=1800 g/mol; PDI=1.0). The polymer had a T/C of 0.212 W/m·K and peak melting point of 78.4° C.

Example 4: Biphenyl Functionalized Polyorganosiloxane Bearing Terminal Methyl Group (A4)

A three-necked flask was charged with 55.2 g of 4-(allyloxy)-1,1'-biphenyl, toluene (90 mL) and platinum catalyst (15 ppm). The resulting mixture was heated to 72° C. while stirring under nitrogen atmosphere and adding 30 g of polydimethylsiloxane having terminal trimethylsiloxy units, approximately 23 methylhydrogensiloxy units and consisting of approximately 16 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as white solid (GPC: $M_n$=6400 g/mol; PDI=1.9). The polymer had a T/C of 0.194 W/m·K and peak melting point of 55.1° C.

Example 5: Biphenyl Functionalized Organosiloxane Bearing T Structure (A5)

A three-necked flask was charged with 39.4 g of 4-(allyloxy)-1,1'-biphenyl, toluene (90 mL) and platinum catalyst (15 ppm). The resulting mixture was heated to 72° C. while stirring under nitrogen atmosphere and adding 20 g of 3-((dimethylsilyl)oxy)-1,1,5,5-tetramethyl-3-phenyltrisiloxane. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane resin as white waxy solid (GPC: $M_n$=800 g/mol; PDI=1.0). The polymer had a T/C of 0.181 W/m·K and peak melting point of 29.3° C.

Example 6: Polyorganosiloxane Bearing Terminal Allyloxy Biphenyl Ether Group (A6)

A three-necked flask was charged with 7.8 g of 4,4'-(bisallyloxy)-1,1'-biphenyl, toluene (90 mL) and platinum catalyst (15 ppm). The resulting mixture was heated to 75° C. while stirring under nitrogen atmosphere and adding 100 g of polydimethylsiloxane having terminal dimethylhydrogensiloxy units and consisting of approximately 100 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as a soft waxy material (GPC: $M_n$=14600 g/mol; PDI=1.5) which has peak melting point of 96° C.

Example 6a: Biphenyl Functionalized Polyorganosiloxane Bearing Terminal Biphenyl Ether Group (A6a)

A three-necked flask was charged with 26.8 g of 4-(allyloxy)-1,1'-biphenyl, toluene (90 mL) and platinum catalyst (15 ppm). The resulting mixture was heated to 72° C. while stirring under nitrogen atmosphere and adding 50 g of polydimethylsiloxane having terminal dimethylhydrogensiloxy units, approximately 8 methylhydrogensiloxy units and consisting of approximately 48 condensed dimethylsiloxy units. The progress of the reaction mixture was monitored by $^1$H NMR. After completion of the reaction, the resulting mixture was vacuum stripped to remove volatiles by placing on a oil bath at 140° C. for 3 h, which gave arylene ether substituted siloxane polymer as gummy material (GPC: $M_n$=4500 g/mol; PDI=2.0). The polymer had a T/C of 0.192 W/m·K and peak melting point of 24.7° C.

Composition

Alumina oxide fillers of average particle size varying from 0.2-12 micron were purchased from Sumitomo and those from 10-120 micron were purchased from Showa Denko. Boron nitride (BN) fillers of size ranging from 5 to 350 micron and morphology were procured from Momentive Performance Materials.

Phase change thermal interface silicone compositions were prepared by mixing the polymers obtained in the synthesis examples (A1 to A6a), antioxidants, inhibitors, coupling agents and fillers as shown in Table 1. The components other than fillers were mixed and was heated up to 150° C. to melt polymer and fillers were added to it and blended it thoroughly. The composition was cooled to room temperature and the bulk thermal conductivity were measured. Control test (Ex-10) uses a alkylated silicone wax (B1) as the polymer.

TABLE 1

| Composition | Polymer | Polymer (wt %) | Antioxidant (wt %) | Coupling agent (wt %) | Alumina* (wt %) | T/C (W/m · K) |
|---|---|---|---|---|---|---|
| Ex-7 | A1 | 10 | 0 | 0 | 90 | 3.3 |
| Ex-8 | A2 | 10 | 0 | 0 | 90 | 3.2 |
| Ex-9 | A6 | 10 | 0 | 0 | 90 | 2.7 |
| Ex-10 | B1 | 10 | 0 | 0 | 90 | 4.6 |
| Ex-11 | A6 | 9 | 1 | 0 | 90 | 3.1 |
| Ex-12 | A6 | 8 | 2 | 0 | 90 | 3.3 |
| Ex-13 | A6 | 7.8 | 2 | 2 | 88.2** | 2.2 |

*Spherical morphology; 0.4-1μ/2-10μ/10-120μ = (20/20/60),
**0.4-1μ/2-10μ/10-120μ = (22/78/0).

Thermal conductivity results of the phase change thermally conducting composition polyorganosiloxane (A1 to A6a) and combination of spherical alumina and boron nitride of platelet and agglomerated morphology are reported in Table 2.

| Compositions* | Ex-14 | Ex-15 | Ex-16 | Ex-17 | Ex-18 | Ex-19 |
|---|---|---|---|---|---|---|
| Polymer | 10.8 (A3) | 10.4 (A4) | 12.6 (A5) | 6.0 (A6) | 9.8 (A6) | 4.2 (A6) |
| Antioxidant | 2 | 2 | 2.4 | 2 | 2 | 2 |
| Coupling agent | 2.2 | 2.3 | 2.8 | 2 | 2.3 | 2 |
| Alumina** (0.2-1μ) | 14.4 | 14.0 | 16.9 | 30 | 14.1 | 18.6 |
| Alumina** (2-5μ) | 28.9 | 28.2 | 34.1 | 60 | 28.4 | 18.6 |
| Alumina** (10-120μ) | 0 | 0 | 0 | | 0 | 55.8 |
| BN# (30-60μ) | 8.9 | 8.6 | 10.4 | | 8.7 | 0 |
| BN## (100-400μ) | 32.8 | 34.5 | 20.8 | 0 | 34.7 | 0 |
| T/C (W/m · K) | 5.6 | 8.7 | 4.7 | 2.9 | 7.9 | 5.8 |

*Composition in wt %,
**Spherical morphology,
Platelet morphology
Agglomerated morphology.

The thermal transition of the phase change silicone composition 3 was probed by testing the viscosity vs temperature as reported in Table 3. Viscosity is measured by TA Instruments Inc. (DHR-3) rheometer using parallel plate geometry at shear rate 2.5 s$^{-1}$.

TABLE 3

| | | Viscosity (Pa · s) | | | | | |
|---|---|---|---|---|---|---|---|
| Entry | Composition | 25 (° C.) | 40 (° C.) | 60 (° C.) | 80 (° C.) | 100 (° C.) | 120 (° C.) |
| Ex-20 | Ex-9 | | 1807 | 1035 | 288 | 200 | 221 |
| Ex-21 | Ex-13 | 2929 | 595 | 222 | 121 | 146 | |

Printable or Dispenseable Composition

Example 22

A printable or dispensible composition was made by blending 2% solvent to a composition of Ex-9. An observed viscosity of 52 Pa·s at 10 rpm when measured with Brookfield viscometer (LVDV-1 Prime) using spindle s64.

Vertical Thermal Stability of Composition

Example 23

A 2×2 cm size of compositions at about 0.25 mm thickness were applied to aluminum plate. The specimens were placed in an oven maintained at a specific temperature at an angle of 90° for 96 h. The test is considered as pass if the composition does not migrate or flow under the condition. The composition passed the test at 100, 120, 150 and 200° C. The control sample (Ex-10) failed at 100° C.

Thermal Stability of Composition by Open Baking

The composition is kept in an oven at 150° C. in a container and hardness were tested after certain duration. The hardness of the composition was measured using ASTM D2240 Type durometer (Type E). The test is considered as pass when there is less than 20% change in the initial hardness of the composition.

Example 24

The composition from Ex-12 was kept in over set at 150° C. for 1000 h had a hardness of 26 (shore E) with respect to initial hardness of 28 (Shore E).

As shown in the data, the present polymers allow for an increase in thermal conductivity of a composition. As shown in the data, even a small increase in the amount of filler material can result in a relatively significant increase in the thermal conductivity.

While the above description contains many specifics, these specifics should not be construed as limitations on the scope of the invention, but merely as exemplifications of preferred embodiments thereof. Those skilled in the art may envision many other possible variations that are within the scope and spirit of the invention as defined by the claims appended hereto.

What is claimed is:

1. A phase change composition comprising:
(A) a silicone polymer of the Formula (I):

$$M^1_a M^2_b M^3_c D^1_d D^2_e D^3_f T^1_g T^2_h T^3_i Q_j.$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1$, $R^2$, $R^3$, $R^5$, $R^6$, $R^8$, $R^9$, $R^{10}$, $R^{11}$, $R^{13}$, $R^{15}$, $R^{16}$ are independently selected from a hydrogen, a $C_1$-$C_{60}$ aliphatic or aromatic group, or $C_1$-$C_{60}$ alkoxy group;

$R^4$, $R^{12}$, $R^{17}$ are independently selected from a C1-C10 alkyl, a C1-C10 alkoxy, or $R^{19}$-A-$R^{20}$—, with the proviso that at least one of $R^4$, $R^{12}$, or $R^{17}$ is $R^{19}$-A-$R^{20}$—, where A is selected from a-group of the formula -$A^1$-$R^{21}$-$A^2$– where $A^1$ and $A^2$ are independently selected from a C6 to C12 aryl group, C12-C36 fused aromatic ring group, a C5-C36 unsaturated alicyclic group, or a C5-C36 unsaturated heterocyclic group; and $R^{21}$ is selected from a direct bond, —($CH_2$)$_n$—, —C($CH_3$)$_2$—, —O—, —S—, —S(O)$_2$—, —C(O)—, C(O)—NH—, —NH—C(O)—NH—, C(O)—O—, —CH=N—, or —CH=N—N=CH— where n is 1-10; $R^{19}$ is selected from a —H, a C1-C10 alkyl or allyl or aryl or vinyl optionally containing heteroatom(s), acrylate, or methacrylate; and $R^{20}$ is selected from a divalent organic group;

$R^7$, $R^{14}$, $R^{18}$ are independently selected from hydrogen, $OR^{22}$, an unsaturated monovalent radical, a radical containing a heteroatom selected from oxygen, nitrogen, or sulfur, or a radical containing an organosilane group, where $R^{22}$ is selected from selected from hydrogen or an aliphatic or aromatic monovalent hydrocarbon having from 1 to 60 carbon atoms: and the subscripts a, b, c, d, e, f, g, h, i, j are zero or positive subject to the following limitations: 2≤a+b+c+d+e+f+g+h+i+j≤1000, b+e+h>0 and c+f+i≥0;

B) a thermally conductive filler;
C) optionally an antioxidant;
D) optionally an inhibitor;
E) optionally a volatile diluent; and
F) optionally a coupling agent;

wherein the composition has a phase change temperature of from 30° C. to 120° C.

2. The composition of claim 1, wherein A is independently selected from

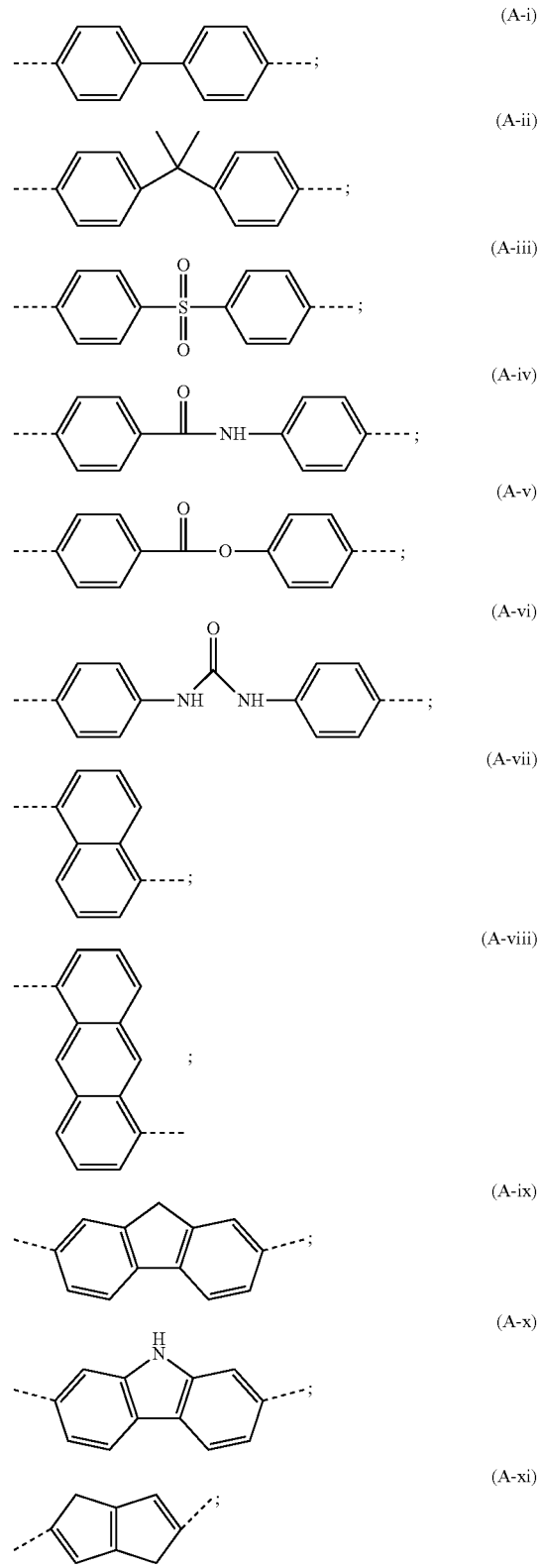

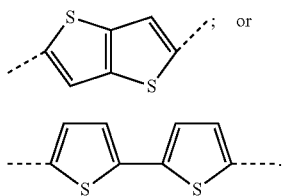 (A-xii)

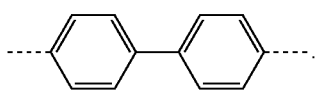 (A-xiii)

3. The composition of claim 1, wherein A in $R^4$, $R^{12}$ and $R^{17}$ is

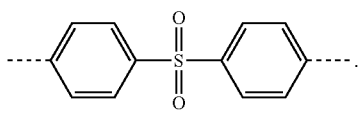

4. The composition of claim 1, wherein $R^{19}$ is $CH_2$=$CH_2$—$(CH_2)_l$—O—and 1 is 0 or 1.

5. The composition of claim 1, wherein $R^1$, $R^2$, $R^3$, $R^5$, $R^6$, $R^8$, $R^9$, $R^{10}$, $R^{11}$, $R^{13}$, $R^{15}$, and $R^{16}$ are methyl.

6. The composition of claim 1, wherein A in $R^4$, $R^{12}$ and $R^{17}$ is

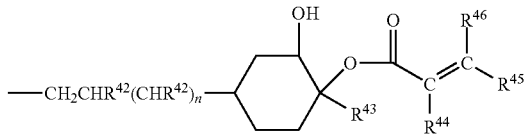

7. The composition of claim 1, wherein $R^{19}$ is selected from —H, $CH_2$=$CH_2$—$(CH_2)_l$—, or $CH_2$=$CH_2$—$(CH_2)_l$—O— where 1 is 0-10; and $R^{20}$ is chosen from a C2-C10 bivalent alkyl group, —O—$(CH_2)_m$—, or —O—C(O)—$(CH2)_m$—, and m is 2-10.

8. The composition of claim 1, wherein the unsaturated monovalent radical is selected from

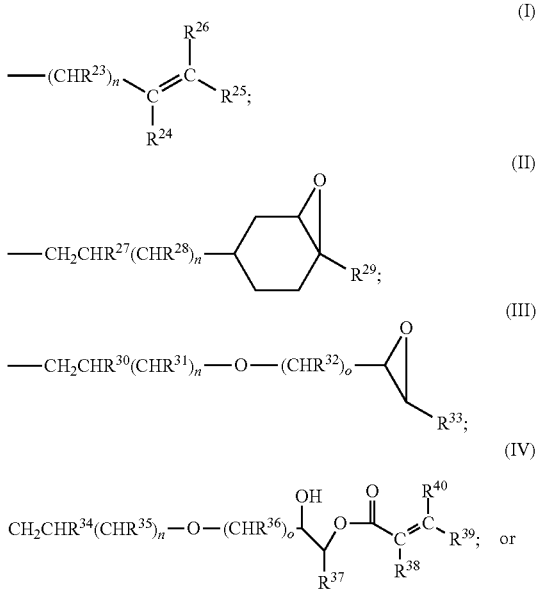

wherein $R^{23}$, $R^{28}$, $R^{31}$, $R^{32}$, $R^{35}$, $R^{36}$, $R^{42}$ are independently selected from —H, —OH, alkyl, alkenyl, cycloalkyl, aryl and aliphatic/aromatic monovalent hydrocarbon having from 1 to 60 carbon atoms; $R^{22}$, $R^{24}$, $R^{25}$, $R^{26}$, $R^{27}$, $R^{29}$, $R^{30}$, $R^{33}$, $R^{34}$, $R^{37}$, $R^{38}$, R39, $R^{40}$, $R^{41}$, $R^{43}$, $R^{44}$, $R^{45}$, $R^{46}$ are independently selected from hydrogen or aliphatic/aromatic monovalent hydrocarbon having from 1 to 60 carbon atoms; the subscript n is zero or positive integer and has a value in the range of 0 to 6; subscript o is positive integer and has a value in the range of 1 to 6.

9. The composition of claim 1 wherein the polymer has a number average molecular weight ($M_n$) of from about 400 g/mol to about 100000 g/mol.

10. The composition of claim 1, wherein the filler material is selected from alumina, magnesia, ceria, hafnia, lanthanum oxide, neodymium oxide, samaria, praseodymium oxide, thoria, urania, yttria, zinc oxide, zirconia, silicon aluminum oxynitride, borosilicate glasses, barium titanate, silicon carbide, silica, boron carbide, titanium carbide, zirconium carbide, boron nitride, silicon nitride, aluminum nitride, titanium nitride, zirconium nitride, zirconium boride, titanium diboride, aluminum dodecaboride, barytes, barium sulfate, asbestos, barite, diatomite, feldspar, gypsum, hormite, kaolin, mica, nepheline syenite, perlite, phyrophyllite, smectite, talc, vermiculite, zeolite, calcite, calcium carbonate, wollastonite, calcium metasilicate, clay, aluminum silicate, talc, magnesium aluminum silicate, hydrated alumina, hydrated aluminum oxide, silica, silicon dioxide, titanium dioxide, glass fibers, glass flake, clays, exfoliated clays, calcium carbonate, zinc oxide, magnesia, titania, calcium carbonate, talc, mica, wollastonite, alumina, aluminum nitride, graphite, graphene, aluminum powder, copper powder, bronze powder, brass powder, fibers or whiskers of carbon, graphite, silicon carbide, silicon nitride, alumina, aluminum nitride, zinc oxide, carbon nanotubes, boron nitride nanosheets, zinc oxide nanotubes, or a combination of two or more thereof.

11. The composition of claim 10, wherein the filler material has a mean particle size of from about 0.01 μm to about 500 μm.

12. The composition of claim 1 wherein the filler material is selected from a plurality of filler materials.

13. The composition of claim 1, wherein the filler material is selected from a first filler having an average particle size from about 0.01 to about 0.9 μm; a second filler having an average particle size of about 1 μm to about 10 μm; a third filler having an average particle size of about 15 μm to about 150 μm; and optionally a fourth filler having an average particle size of about 100 μm to about 400 μm.

14. The composition of claim 1 comprising about 10 vol. % to about 90 vol. % of the first filler and about 90 vol. % to about 10 vol. % of the second filler.

15. The composition of claim 1, wherein the filler comprises (i) a first filler, and (ii) a second filler, where at least one of the first filler and the second filler comprises a plurality of filler types differing from one another in terms of particle size and/or morphology.

16. The composition of claim 15, wherein the first and second filler are independently selected from a metal oxide filler or a non-oxide filler.

17. The composition of claim 16, wherein the non-oxide filler is selected from a metal boride, a metal carbide, a metal nitride, a metal silicide, carbon black, graphite, expanded graphite, carbon fiber, graphite fiber, or a combination of two or more thereof.

18. The composition of claim 15, wherein the plurality of filler types independently have an average particle size of from about 0.3 micron to about 350 micron, the plurality of filler types having average particle sizes different from one another.

19. The composition of claim 15, wherein the plurality of filler types have a morphology different from one another, the morphology being selected from spherical, platelet, agglomerates, spherical agglomerates, or graphitic.

20. The composition of claim 15, wherein the first filler is selected from aluminum oxide, and the second filler is select from boron nitride.

21. The composition of claim 20, wherein the aluminum oxide comprises a plurality of filler types.

22. The composition of claim 21, wherein the plurality of filler types have an average particle size different from one another.

23. The composition of claim 21, wherein the plurality of filler types have a morphology different from one another.

24. The composition of claim 20, wherein the aluminum oxide and the boron nitride each comprises the plurality of filler type.

25. The composition of claim 1, where the composition has a thermal conductivity in the range of 2 to 18 W/m.K.

26. The composition of claim 1, where the composition has a thermal stability till 200° C. for 1500 hrs.

27. The composition of claim 1 in the form of a thermal grease, adhesive, thermal gel, potting material, or a gap filler material.

28. An article comprising the composition of claim 1 disposed on at least a portion of a surface of the article.

29. The article of claim 28, wherein the article comprises multiple layers, and the composition is disposed on a surface in between at least two of the layers.

30. The article of claim 28, wherein the article is an electronic article, an automotive article, a home appliance article, smart appliance article, a telecommunication article, a healthcare article, a personal care article, an agricultural article, a molded article, a masonry surface, a textile material, or a home care material.

31. The article of claim 28, wherein the article is a light emitting device, a computer device, a stacked die, a mobile phone, a tablet, a flip chip package, a hybrid memory cube, a touch screen, a Wi-Fi device, an automotive technology Hi-Fi system, a through-silicon via device, audio system, a joint between heat pipes and water tanks in solar heated heating, a fuel cell, a wind turbine, a computer chip, a gaming console, a data transfer device, a light device, a battery, a housing, a cooler, a heat exchanging device, a wire, a cable, a heating wire, a refrigerator, a dishwasher, an air conditioniner, an accumulator, a transformer, a laser, functional clothin, a car seat, a medical device, a fire protection device, an electric motor, a plane, a train, as a filament for 3D printing material, a drug delivery system, a transdermal patch, a wound healing patch, a wound dressing patch, a patch for scar reduction, transdermal iontophoresis, a scaffold for tissue engineering, an anti-microbial device, a wound management device, an ophthalmic device, a bioinsert, a prostheses, a body implant, paint, a structural coating, a masonry coating, a marine coating, a seed coating, a superspreader, or a controlled release fertilizer.

32. A method of preparing the article of claim 28 comprising of dispensing under pressure or stencil printing or screen printing or jet printing or 3D printing.

33. The method of preparation of article of 28 wherein thickness of the said composition is from 0.01 mm to 15 cm.

34. A personal care product comprising the composition of claim 1.

35. The personal care product of claim 34 in the form of an antiperspirant/deodorant, a shaving product, a skin lotion, a moisturizer, a toner, a bath product, a cleansing product, a shampoo, a conditioner, a combined shampoo/conditioners, a mousse, a styling gel, a hair spray, a hair dye, a hair color product, a hair bleach, a waving products, a hair straightener, a nail polish, a nail polish remover, a nail cream or lotions, a cuticle softener, a sunscreen, an insect repellent, an anti-aging product, a lipstick, a foundation, a face powder, an eye liner, an eye shadow, a blush, a makeup, a mascara, a moisturizing preparation, a foundation, a body and hand preparation, a skin care preparation, a face and neck preparation, a tonic, a dressing, a hair grooming aid, an aerosol fixative, a fragrance preparation, an aftershave, a make-up preparation, a soft focus application, a night and day skin care preparation, a non-coloring hair preparation, a tanning preparation, a synthetic and non-synthetic soap bar, a hand liquid, a nose strip, a non-woven application for personal care, a baby lotion, a baby shampoo, a baby conditioner, a shaving preparation, a cucumber slices, a skin pads, a make-up remover, a facial cleansing product, a cold cream, a sunscreen product, a spritzer, a paste mask and mud, a face mask, a cologne and toilet water, a hair cuticle coat, a shower gel, a face and body wash, a personal care rinse-off products, a gel, a foam bath, a scrubbing cleanser, an astringent, a nail conditioner, an eye shadow stick, a powder for face or eye, a lip balm, a lip gloss, a hair care pump spray, a hair-frizz-control gel, a hair leave-in conditioner, a hair pomade, a hair de-tangling product, a hair fixative, a hair bleach product, a skin lotion, a pre-shave and pre-electric shave, an anhydrous cream and lotion, an oil/water emulsion, a water/oil emulsion, a water-resistant cream or lotion, an anti-acne preparation, a mouth-wash, a massage oil, a toothpaste, a clear gel or stick, an ointment base, a topical wound-healing product, an aerosol talc, a barrier spray, a vitamin or anti-aging preparation, an herbal-extract preparation, a bath salt, a bath and body milk, a hair styling aid, a hair-, eye-, nail- and skin-soft solid application, a controlled-release personal care product, a hair conditioning mist, a skin care moisturizing mist, a skin wipe, a pore skin wipe, a pore cleaner, a blemish reducer, a skin exfoliator, a skin desquamation enhancer, a skin towelette or cloth, a depilatory preparation, or a personal care lubricant.

36. A process for preparing composition of claim 1 comprising:
a) providing a silicone polymer of Formula (I)

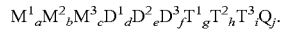

wherein:
$M^1 = R^1R^2R^3SiO_{1/2}$
$M^2 = R^4R^5R^6SiO_{1/2}$
$M^3 = R^7R^8R^9SiO_{1/2}$
$D^1 = R^{10}R^{11}SiO_{2/2}$
$D^2 = R^{12}R^{13}SiO_{2/2}$
$D^3 = R^{14}R^{15}SiO_{2/2}$
$T^1 = R^{16}SiO_{3/2}$
$T^2 = R^{17}SiO_{3/2}$
$T^3 = R^{18}SiO_{3/2}$
$Q = SiO_{4/2}$

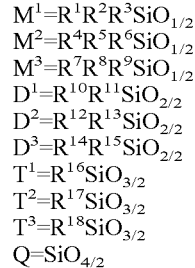

where $R^1, R^2, R^3, R^5, R^6, R^8, R^9, R^{10}, R^{11}, R^{13}, R^{15}, R^{16}$ are independently selected from a hydrogen, a $C_1$-$C_{60}$ aliphatic or aromatic group, or $C_1$-$C_{60}$ alkoxy group;

$R^4, R^{12}, R^{17}$ are independently selected from a C1-C10 alkyl, a C1-C10 alkoxy, or $R^{19}$-A-$R^{20}$— where A is selected from a group comprising an unsaturated cyclic moiety selected from an aromatic group, a fused aromatic group, an unsaturated alicyclic group, an unsaturated heterocyclic group, or a combination of two or more thereof; $R^{19}$ is selected from a —H, a C1-C10 alkyl, allyl, vinyl, alkoxy, allyloxy, vinyloxy, acrylate, or methacrylate; and $R^{20}$ is selected from a divalent organic group;

$R^7, R^{14}, R^{18}$ are independently selected from hydrogen, $OR^{22}$, an unsaturated monovalent radical, a radical containing a heteroatom selected from oxygen, nitrogen, or sulfur, or a radical containing an organosilane group, where $R^{22}$ is selected from selected from hydrogen or an aliphatic or aromatic monovalent hydrocarbon having from 1 to 60 carbon atoms; and the subscripts a, b, c, d, e, f, g, h, i, j are zero or positive subject to the following limitations: $2 \leq a+b+c+d+e+f+g+h+i+j \leq 1000$, $b+e+h>0$ and $c+f+i \geq 0$;

b) optionally add an inhibitor, an antioxidant, a coupling agent, or a combination thereof to (a);
c) add a thermally conductive filler to the mixture;
e) optionally add a volatile diluent before or after adding the thermal filler.

* * * * *